US012746256B2

(12) United States Patent
Thomas, Sr.

(10) Patent No.: US 12,746,256 B2
(45) Date of Patent: Sep. 29, 2026

(54) TOPICAL COMPOSITION FOR TREATMENT OF PAIN AND SYMPTOMS ASSOCIATED WITH RHINOSINUSITIS, METHOD OF MAKING, AND METHOD OF USE

(71) Applicant: THREE FIFTHS, LLC, Foley, AL (US)

(72) Inventor: Brian D. Thomas, Sr., Foley, AL (US)

(73) Assignee: THREE FIFTHS, LLC, Foley, AL (US)

( * ) Notice: Subject to any disclaimer, the term of this patent is extended or adjusted under 35 U.S.C. 154(b) by 917 days.

(21) Appl. No.: 17/343,233

(22) Filed: Jun. 9, 2021

(65) Prior Publication Data

US 2021/0290665 A1 Sep. 23, 2021

Related U.S. Application Data

(63) Continuation-in-part of application No. PCT/US2019/064885, filed on Dec. 6, 2019.

(51) Int. Cl.

| | |
|---|---|
| ***A61K 33/14*** | (2006.01) |
| ***A61K 9/00*** | (2006.01) |
| ***A61K 31/194*** | (2006.01) |
| ***A61K 47/46*** | (2006.01) |
| ***A61P 29/00*** | (2006.01) |

(52) U.S. Cl.

CPC ............ *A61K 33/14* (2013.01); *A61K 9/0014* (2013.01); *A61K 31/194* (2013.01); *A61K 47/46* (2013.01); *A61P 29/00* (2018.01)

(58) Field of Classification Search

CPC .... A61K 33/14; A61K 9/0014; A61K 31/194; A61K 47/46; A61P 29/00

See application file for complete search history.

(56) References Cited

U.S. PATENT DOCUMENTS

| | | | | |
|---|---|---|---|---|
| 5,980,880 | A | 11/1999 | Love | |
| 2004/0209852 | A1* | 10/2004 | Chaudry ................ | A61K 31/57 424/46 |
| 2014/0356288 | A1 | 12/2014 | Kirkpatrick et al. | |

FOREIGN PATENT DOCUMENTS

| | | | |
|---|---|---|---|
| WO | WO 00/16752 | A2 | 3/2000 |

OTHER PUBLICATIONS

Mightynest, The Essential: 6 uses for peppermint essential oil, 2016, Mightynest.com; from https://mightynest.com/articles/the-essential-6-uses-for-peppermint-essential-oil (Year: 2016).*

Corn Products, Naturally improving sensorial attributes with corn starch, 2013, Cosmetics and Toiletries; fromhttps://www.cosmeticsandtoiletries.com/cosmetic-ingredients/sensory/article/21836185/naturally-improving-sensorial-attributes-with-corn-starch (Year: 2013).*

Cleveland Clinic, "How Aromatherapy Can Help Ease Your Pain", Jun. 1, 2016, total 3 pages.

International Search Report, issued in PCT/US2019/064885, PCT/ISA/210, dated Apr. 6, 2020.

University Federico II of Naples, "Starch", Jun. 1, 2017, total 1 page.

Wikipedia, "Sea Salt", Sep. 19, 2018, p. 1-4.

Written Opinion of the International Searching Authority, issued in PCT/US2019/064885, PCT/ISA/237, dated Apr. 6, 2020.

* cited by examiner

*Primary Examiner* — Isis A Ghali
*Assistant Examiner* — Ayaan A Alam
(74) *Attorney, Agent, or Firm* — Birch, Stewart, Kolasch & Birch, LLP

(57) ABSTRACT

A topical composition for the treatment of pain includes a hydrophilic carrier; a therapeutically active ingredient of potassium bitartrate and at least one of potassium chloride, calcium chloride, and magnesium chloride; at least one essential oil; and water.

17 Claims, No Drawings

TOPICAL COMPOSITION FOR TREATMENT OF PAIN AND SYMPTOMS ASSOCIATED WITH RHINOSINUSITIS, METHOD OF MAKING, AND METHOD OF USE

CROSS-REFERENCE TO RELATED APPLICATIONS

This application is a Continuation-in-part of PCT International Application No. PCT/US2019/064885, filed on Dec. 6, 2019, which is hereby expressly incorporated by reference into the present application.

BACKGROUND OF THE INVENTION

1. Field of the Invention

The present invention relates to a topical composition for treatment of pain and relief of symptoms associated with Rhinosinusitis and method of use thereof. In particular, the method comprises a topical composition for the treatment of pain and relief of symptoms associated with Rhinosinusitis (symptoms) comprising a hydrophilic carrier; a therapeutically active ingredient comprising potassium bitartrate and at least one of potassium chloride, calcium chloride, and magnesium chloride; at least one essential oil; and water.

2. Description of the Background Art

The search for more effective topical inflammation and/or pain and Rhinosinusitis symptom relief agents than those known at present is a never-ending one. Efforts are constantly being made to find compositions, which by topical application, will rapidly alleviate pain, such as rheumatic muscular and joint aches and pains; allergy symptoms such as sneezing, sinus congestion and headache; and premenstrual symptoms like pain and cramping. Many compositions have been formulated for topical application to relieve such symptoms, but many of these compositions have the disadvantage of requiring intense rubbing or massaging of the material into the skin or membrane (surface) in order to effect penetration of the active ingredient, a major challenge when suffering from hand or finger pain or if the symptom locale is difficult to reach. This lack of rapid penetration of the active symptom-relieving ingredients prolongs discomfort and delays the desired relief. Where penetration of the active ingredients is resisted by the surface, only a minor symptom-relieving effect results. Such compositions also require the application of large quantities of the material in order to obtain relief, which of course causes discomfort to the user.

The present invention addresses the deficiencies of the conventional art. In this regard, the present invention relates to topical compositions for temporary, rapid relief of acute and chronic pain and Rhinosinusitis and/or symptoms accompanying or caused by inflammation. Such symptoms include, but are not limited to, muscle pain, joint pain, tendonitis, respiratory distress (sinus and bronchial), premenstrual symptoms, and headache. More particularly, the present invention relates to potassium salt/essential oil-based compositions for topical application having a combination of potassium bitartrate and potassium chloride; and at least one essential oil having symptom relief properties as the therapeutically active ingredients to effect rapid penetration by the active ingredients into the skin to provide for quick symptom relief.

SUMMARY OF THE INVENTION

One embodiment of the present invention is directed to a topical composition for the treatment of pain and relief of Rhinosinusitis symptoms (symptoms), comprising a hydrophilic carrier; a therapeutically active ingredient comprising potassium bitartrate and at least one of potassium chloride, calcium chloride, and magnesium chloride; at least one essential oil; and water.

The hydrophilic carrier may comprise at least one of yellow mustard, lecithin, fatty acid esters, sodium stearoyl lactylate, ethoxylated alcohols, carboxylates, sodium isethionate, glycerol monostearate, cetyl alcohol, stearyl alcohol, silicone emulsifiers, or polyelectrolytes. The hydrophilic carrier may be a sprayable carrier and the topical composition may be a spray. In this case, the hydrophilic carrier may be combined with a dispensing gas. The dispensing gas may be an inert gas, such as argon. The therapeutically active ingredient may comprise potassium bitartrate and potassium chloride. The at least one essential oil may comprise at least one oil derived from lavender, eucalyptus, peppermint, rosemary, patchouli, lemon, sweet orange, clary sage, tea tree, ylang ylang, coconut, olive, castor, menthol, crisp mint, spearmint, or aloe. The topical composition may also comprise at least one of a parasept, a coolant, a perfume, or a surfactant. The topical composition may be in the form of a liquid, paste, cream, ointment, gel, lotion, spray, soft capsule, solution, or transdermal patch.

Another embodiment of the present invention is directed to a method for making a topical composition, comprising mixing potassium bitartrate; at least one of potassium chloride, calcium chloride, and magnesium chloride; and at least one essential oil with water to form a homogeneous mixture; incubating the homogeneous mixture; and incorporating the incubated mixture into a hydrophilic carrier.

A different method for making a topical composition comprises mixing potassium bitartrate; at least one of potassium chloride, calcium chloride, and magnesium chloride; at least one essential oil; and a hydrophilic carrier with water to form a homogeneous mixture; and incubating the homogeneous mixture.

In either method for making the topical composition, the homogeneous mixture may be incubated at a temperature of 25° C. to 32° C. and for a time period of 24 hours to 3 weeks. The at least one of potassium chloride, calcium chloride, and magnesium chloride may be at least potassium chloride.

Another embodiment of the present invention is directed to a method for treating pain in a subject, comprising applying a therapeutically effective amount of a topical composition to skin of the subject; wherein the topical composition comprises a hydrophilic carrier; a therapeutically active ingredient comprising potassium bitartrate and at least one of potassium chloride, calcium chloride, and magnesium chloride; at least one essential oil; and water.

In this embodiment, the pain may be at least one of chronic rheumatic pain, pain due to sinus congestion and/or pressure, headaches, ear pressure/pain, bronchial constriction, premenstrual symptoms, muscle soreness, fibromyalgia, and acute pains due to sprains or strains. The at least one of potassium chloride, calcium chloride, and magnesium chloride may be at least potassium chloride.

Another embodiment of the present invention is directed to a method for treating symptoms of Rhinosinusitis in a subject, comprising applying a therapeutically effective amount of a topical composition to membranes of the nasal passages of the subject; wherein the topical composition comprises a hydrophilic carrier; a therapeutically active ingredient comprising potassium bitartrate and at least one of potassium chloride, calcium chloride, and magnesium chloride; at least one essential oil; and water.

In this embodiment, the symptoms may be at least one of sneezing, an itchy, runny or blocked nose (allergic rhinitis), itchy, red, watering eyes (conjunctivitis), and pain due to sinus congestion and/or pressure. The at least one of potassium chloride, calcium chloride, and magnesium chloride may be at least potassium chloride.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to one of ordinary skill in the art from this detailed description.

DETAILED DESCRIPTION OF THE INVENTION

The present invention is directed to a topical composition for treatment of pain, a method of making the topical composition, and a method of use of the topical composition.

(1) Topical Composition

The present invention resides in the discovery of a topical composition having rapid tissue penetrating powers to bring about increased effectiveness for the relief of symptoms caused by inflammation. The topical compositions of the present invention unexpectedly allow active ingredients to be delivered directly to deeper targeted sites, eliminating the need for injections or systemic oral medications that may present safety concerns. The topical compositions have the capability to readily penetrate into and through the skin and underlying tissue. The topical composition for the treatment of pain comprises a hydrophilic carrier; a therapeutically active ingredient comprising potassium bitartrate and at least one of potassium chloride, calcium chloride, and magnesium chloride (preferably potassium chloride); at least one essential oil; and water.

The hydrophilic carrier is not generally limited and may be any hydrophilic carrier known in the art. Examples of the hydrophilic carrier include any type of hydrophilic base, such as an ointment, a cream, a petrochemical base, a base comprised of polymerized resins capable of emulsification, or an aliphatic base. It will be appreciated that these bases act as the carrier of the active ingredients and present a homogeneous medium with the active ingredients thoroughly dispersed therethrough so that application to the body effects uniform medication to the area treated. Such hydrophilic carriers are readily available. Examples of the hydrophilic carrier include yellow mustard, lecithin, fatty acid esters, sodium stearoyl lactylate, ethoxylated alcohols, carboxylates, sodium isethionate, glycerol monostearate, cetyl alcohol, stearyl alcohol, silicone emulsifiers such as dimethicones, and polyelectrolytes, such as sodium polyacrylate. These hydrophilic carriers may be combined with thickeners, humectants, preservatives, neutralizers, occlusive agents, and fragrances to produce a wide variety of effective topical applications.

The amount of hydrophilic carrier in the topical composition is not generally limited but may be about 1% to about 10% by volume of the topical composition, preferably 2% to 6% by volume of the topical composition.

In another embodiment, the hydrophilic carrier may be a sprayable carrier for treatment of the body so that the topical composition is a spray. The sprayable carrier is not generally limited and may be any sprayable carrier known in the art. For example, the hydrophilic carrier may be a sprayable type of base that allows for application of a drug to the human body from a pressurized dispensing device having the ability to apply the spray in a simple and effective manner. In this type of applicator, the carrier may be combined with a dispensing gas that will produce a non-foaming application of the effective ingredients.

The dispensing gas is not generally limited and may be any dispensing gas known in the art. The dispensing gas may be an inert gas. The inert gas is preferably argon, which minimizes the possibility of foaming. Argon gas does not form a foamable mixture with many materials to be sprayed when it is released from the pressurized container. Rather, argon acts like a piston so that the composition is projected for effective application to the skin. Other types of dispensing gas include nitrous oxide and carbon dioxide.

The amount of hydrophilic carrier as a sprayable carrier in the topical composition is not generally limited but may be about 1% to about 10% by volume of the topical composition, preferably 2% to 6% by volume of the topical composition. The amount of dispensing gas in the topical composition is not generally limited but may be about 5% to 95% by volume of the topical composition.

The therapeutically active ingredient comprises potassium bitartrate (also known as cream of tartar) and at least one of potassium chloride, calcium chloride, and magnesium chloride (preferably potassium chloride). These components are readily available.

The amount of potassium bitartrate is not generally limited but may be about 0.2% to about 3% by volume of the topical composition, preferably 0.5 to 1 percent by volume of the topical composition.

The total amount of the at least one of potassium chloride, calcium chloride, and magnesium chloride is not generally limited but may be about 0.1% to about 5% by volume of the topical composition, preferably 3 to 5 percent by volume of the topical composition. If more than one of potassium chloride, calcium chloride, and magnesium chloride is present in the topical composition, the amounts of each component may be the same or different.

The amounts of potassium bitartrate and at least one of potassium chloride, calcium chloride, and magnesium chloride may be varied in order to achieve the desired therapeutic results.

The essential oil is not generally limited and may be any essential oil known in the art. Examples of essential oil include plant extracts, essences, absolutes, or any other naturally-occurring derivative oil of plants, which imparts a fragrance. Specific examples of essential oils may include, but are not limited to, oils derived from lavender, eucalyptus, peppermint, rosemary, patchouli, lemon, sweet orange, clary sage, tea tree, ylang ylang, coconut, olive, castor, menthol, crisp mint, spearmint, and aloe. Such essential oils are generally readily available. One or more essential oils may be used.

The total amount of the essential oil in the topical composition is not generally limited but may be about 1% to about 20% by volume of the topical composition, preferably 1 to 10 percent by volume of the topical composition. The amount of each individual essential oil in the topical composition is not generally limited but may be about 1% to about 20% by volume of the topical composition, preferably 1 to 10 percent by volume of the topical composition. In other words, one essential oil may comprise the entire essential oil profile, or several oils may comprise the entire essential oil profile. If more than one essential oil is present in the topical composition, the amounts of each essential oil may be the same or different. The amounts of the essential oil(s) may be varied in order to achieve the desired therapeutic results.

The topical composition also includes water. The amount of water is not generally limited and depends on the form of the topical composition. That is, a cream will have less water than a liquid. However, the amount of water may be about 20% to about 97% by volume of the topical composition, preferably about 62 percent to about 97 percent by volume of the topical composition, more preferably 78 to 93 percent by volume of the topical composition.

The topical composition may also optionally include additional ingredients. The additional ingredients include parasepts for preventing fungus growth; coolants; perfumes; surfactants; and other body treating and soothing compounds. Examples of parasepts include Propyl Parasept, Methyl Parasept and Butyl Parasept. Examples of coolants include menthol, thymol, eucalyptol, and camphor.

The topical compositions may contain suitable buffering agents, including acetic acid in a salt; citric acid in a salt; boric acid in a salt; and phosphoric acid in a salt. The topical compositions also may contain, optionally, suitable preservatives, such as benzalkonium chloride; chlorobutanol; parabens, and thimerosal. The compositions may also include a variety of other materials such as solvents, surfactants, thickeners, colorants, and the like. Other additional ingredients include anti-fungal substances such as amorolfine, ciclopirox, oxiconazole, and nystatin.

The total amount of the additional ingredients in the topical composition is not generally limited. However, any additional ingredients would replace an equivalent volume percent of water in the topical composition. Thus, the total amount of water and any additional ingredients may be about 20% to about 97% by volume of the topical composition, preferably about 62 percent to about 97 percent by volume of the topical composition, more preferably 78 to 93 percent by volume of the topical composition. If more than one additional ingredient is present in the topical composition, the amounts of each additional ingredient may be the same or different. It will be appreciated that the percentages of the various additive ingredients, such as the coolants, surfactants, and fungicides (parasepts) may be varied to produce the desired effects depending upon the degree of surface activity required in the composition.

It will be understood that many non-active ingredients other than those illustrated above may be incorporated in the compositions of the present invention to produce a variety of effects.

(2) Method of Making

It has been found that the combination of potassium bitartrate and at least one of potassium chloride, calcium chloride, and magnesium chloride (preferably potassium chloride); and at least one essential oil provides an active ingredient which, when incorporated in water and incubated at 25° C. for 24 hours, produces rapid and uniform penetration of the ingredients into the skin and tissue to bring about quick relief from symptoms caused by inflammation. Faster and greater relief is noted by increasing incubation time up to 3 weeks.

In other words, in one embodiment, the potassium bitartrate, the at least one of potassium chloride, calcium chloride, and magnesium chloride, the at least one essential oil, and optionally any additional ingredients are mixed with water until uniformly distributed and incubated. The amounts of the potassium bitartrate, the at least one of potassium chloride, calcium chloride, and magnesium chloride, the at least one essential oil, the water, and the optional additional ingredients are discussed above.

The incubation temperature is not generally limited and may be 25° C. to 32° C., preferably about 25° C. The incubation time is not generally limited and may be 24 hours to 3 weeks. The topical composition becomes more effective as the incubation time increases up to 3 weeks. Thus, the incubation time is preferably 2-3 weeks, and more preferably about 3 weeks.

The incubated mixture of active ingredients of the present invention may then be incorporated in any type of hydrophilic carrier as identified above in the amounts identified above.

In another embodiment, which changes the order that the ingredients are added, the at least one of potassium chloride, calcium chloride, and magnesium chloride may be dissolved in purified water. Then, the hydrophilic carrier may be added. Next, the potassium bitartrate, one or more essential oils, and any optional additional ingredients may be added. The mixture is then mixed until homogeneous. This mixture is then incubated.

If the incubated mixture of active ingredients of the present invention is to be applied as a spray by incorporating it in a sprayable carrier for treatment of the body, a simple pump spray providing adequate atomization of the homogenous liquid can be used. As discussed above, in this embodiment, the hydrophilic carrier may be a sprayable type of base that allows for application of a drug to the human body from a pressurized dispensing device having the ability to apply the spray in a simple and effective manner. In this type of applicator, the carrier is preferably combined with a dispensing gas, which will produce a non-foaming application of the effective ingredients. A standard pressurized dispensing device may be used to apply the spray to the skin. It has been found previously that a very effective gas, which minimizes the possibility of foaming, is argon, but it will be appreciated that other types of inert gases may be used, as discussed above. It has been found previously that argon gas does not form a foamable mixture with many materials to be sprayed when it is released from the pressurized container. Rather, argon acts like a piston so that the composition is projected for effective application to the skin.

Optionally, additional ingredients may be added to the active ingredients and the hydrophilic carrier. Such additional ingredients are identified above.

(3) Method of Use

It is believed that the rapidity of inflammation symptom relief effected by the compositions of the present invention is mainly the result of esters of bitartrate and essential oil(s) formed in a medium of KCl/water during the incubation period, enhanced by symptom-relieving properties of the individual constituents, themselves. Potassium chloride is used in the preferred embodiment, but any reference to KCl provided herein can be equally applied to potassium chloride, calcium chloride, and magnesium chloride, alone or in any combinations thereof.

The compositions of the present invention may be in form of a solution or in a hydrophilic base, such as a polymerized resin, cream, ointment, salve, or the like. It is believed that the principal active analgesic ingredient in the composition are the esters of bitartrate and essential oil(s) formed in a medium of KCl/water during the incubation period. The other active ingredients are the individual constituents: KCl, potassium bitartrate, and at least one essential oil having symptom relief properties. The combination of these active ingredients provides for rapid absorption of medication into the tissues of the body upon application as well as antiseptic, antibacterial, and germicidal action, which brings about the quick effective medication of the skin to which the active ingredients have been applied, as well as the thorough and rapid penetration of the tissues for effective relief.

Although the proportions of the active ingredients depend upon the application desired, excellent results are obtained when KCl is in the range of 3 to 5 percent by volume, the potassium bitartrate is in the range of 0.5 to 1 percent by volume, and the essential oil(s) is 1 to 10 percent by volume.

In the method of treating symptoms in a subject, the topical composition is applied or sprayed onto the skin or membrane(s) of the subject in the area where symptoms occur.

The topical composition described above is administered in effective amounts. An effective amount is a dosage of the composition sufficient to provide a medically desirably result. The effective amount may vary with the particular condition being treated, the age and physical condition of the subject being treated, the severity of the condition, the duration of the treatment, the nature of the concurrent therapy (if any), the specific route of administration and like factors within the knowledge and expertise of the health practitioner. It is generally preferred that a maximum dose be used (i.e., the highest safe dose according to sound medical judgment).

The topical composition may be applied in one or several administrations per day. In the event that a response in the subject is insufficient at the initial doses applied, higher doses may be employed to the extent that subject tolerance permits. Multiple doses per day are contemplated to achieve appropriate systemic levels of compounds.

The topical composition may be in any form suitable for topical application, such as liquids, pastes, creams, ointments, gels, or lotions. The topical composition may also be in the form of a spray, liquid, soft capsules, solution, pre-treated applicators (e.g., cotton swabs), or transdermal patches.

The types of symptoms that may be treated include, but are not limited to, chronic rheumatic pain, pain due to sinus congestion and/or pressure, headaches, ear pressure/pain, bronchial constriction, premenstrual symptoms (e.g., pain, cramping, and pressure in the lower abdomen and/or lower back), muscle soreness, fibromyalgia, acute pains such as sprains and strains, sneezing, an itchy, runny or blocked nose (allergic rhinitis), and itchy, red, watering eyes (conjunctivitis).

The following examples are by way of illustration and are not to be considered in any way a limitation of the scope of the compositions forming a part of the invention.

EXAMPLES

Example I

Four percent by volume KCl was dissolved in 91 percent by volume purified water. Two percent yellow mustard was added as an emulsifier. One percent by volume of potassium bitartrate, one percent by volume peppermint oil, and one percent by weight coconut oil were added to the mixture and mixed until homogeneous.

After incubating for 24 hours at room temperature (approximately 25° C.), the mixture was shaken well and sprayed on a calf muscle experiencing chronic rheumatic pain. Complete relief was achieved within 5 seconds. The mixture was also sprayed on a lower back and knee experiencing chronic rheumatic pain with immediate and complete relief in both. Symptom relief lasted 3 hours.

Example II

Four percent by volume KCl was dissolved in 39 percent by volume purified water. Two percent yellow mustard was added as an emulsifier.

One percent by volume of potassium bitartrate, one percent by volume each of peppermint oil, coconut oil, castor oil, olive oil, and lavender oil, were added to the mixture and mixed until homogeneous. 10 percent by volume Aloe Vera water and 39% by volume lemon juice were added and mixed until homogeneous.

After incubating for two weeks at room temperature (approximately 25° C.), the mixture was shaken well and sprayed on several anatomical areas affected by allergy symptoms: severe sinus congestion, pressure and pain, severe headache and ear pressure/pain, and severe bronchial constriction. The face (sinuses), temples, back of the neck, behind the ears, chest and upper back were sprayed with the mixture. Complete pain relief, 90% of sinus pressure, and significant relief of bronchial restriction occurred within 10 minutes according to subjective evaluation by the subject based on ease of breathing. Symptom relief lasted at least 4 hours.

Example III

A mixture was prepared as in Example II and was incubated for 3 weeks at room temperature (approximately 25° C.). The mixture was applied, after shaking well, to anatomical areas experiencing acute premenstrual symptoms. Symptoms included pain, cramping, and pressure in the lower abdomen and lower back. These areas were sprayed well with immediate and complete relief from all symptoms.

Example IV

A mixture was prepared as in Example II and was incubated for 3 days at room temperature (approximately 25° C.). The mixture was filtered and applied using a cotton swab, after shaking well, to the nasal membranes of a subject experiencing acute allergic rhinitis and conjunctivitis symptoms. Symptoms included sneezing, an itchy, runny and blocked nose, and itchy, red, watering eyes. These areas were swabbed well with immediate and complete relief from all symptoms. Relief lasted for 16 hours.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method for treating pain and/or Rhinosinusitis symptoms in a subject, comprising:

applying a therapeutically effective amount of a topical composition to skin or membrane(s) of the subject;

wherein the topical composition comprises a homogeneous mixture of a hydrophilic carrier; a therapeutically active ingredient comprising potassium bitartrate and at least one of potassium chloride, calcium chloride, and magnesium chloride; at least one essential oil; and water;

wherein the hydrophilic carrier comprises at least one of yellow mustard, lecithin, fatty acid esters, sodium stearoyl lactylate, ethoxylated alcohols, carboxylates, sodium isethionate, glycerol monostearate, cetyl alcohol, stearyl alcohol, silicone emulsifiers, or polyelectrolytes; and wherein the topical composition has been incubated for 24 hours to 3 weeks at 25° C. to 32° C. in a medium of KCl/water.

2. The method of claim 1, wherein the symptoms are at least one of chronic rheumatic pain, pain due to sinus congestion and/or pressure, headaches, ear pressure/pain, bronchial constriction, premenstrual symptoms, muscle soreness, fibromyalgia, acute pains due to sprains or strains, sneezing, allergic rhinitis, and conjunctivitis.

3. The method of claim 1, wherein the at least one of potassium chloride, calcium chloride, and magnesium chloride is at least potassium chloride.

4. The method of claim 1, wherein the therapeutically active ingredient comprises potassium bitartrate and potassium chloride.

5. The method of claim 1, wherein the at least one essential oil comprises at least one oil derived from lavender, eucalyptus, peppermint, rosemary, patchouli, lemon, sweet orange, clary sage, tea tree, ylang ylang, coconut, olive, castor, menthol, crisp mint, spearmint, or aloe.

6. The method of claim 1, wherein the topical composition is in the form of a liquid, paste, cream, ointment, gel, lotion, spray, soft capsule, solution, pre-treated applicator, or transdermal patch.

7. A method for treating pain and/or Rhinosinusitis symptoms in a subject, comprising:

applying a therapeutically effective amount of a topical composition to skin or membrane(s) of the subject;

wherein the topical composition comprises a homogeneous mixture of a hydrophilic carrier; a therapeutically active ingredient comprising potassium bitartrate and at least one of potassium chloride, calcium chloride, and magnesium chloride; at least one essential oil; and water;

wherein the hydrophilic carrier is a sprayable carrier and the topical composition is a spray; and wherein the topical composition has been incubated for 24 hours to 3 weeks at 25° C. to 32° C. in a medium of KCl/water.

8. The method of claim 7, wherein the hydrophilic carrier is combined with a dispensing gas.

9. The method of claim 8, wherein the dispensing gas is an inert gas.

10. The method of claim 8, wherein the dispensing gas is argon.

11. The method of claim 7, wherein the symptoms are at least one of chronic rheumatic pain, pain due to sinus congestion and/or pressure, headaches, ear pressure/pain, bronchial constriction, premenstrual symptoms, muscle soreness, fibromyalgia, acute pains due to sprains or strains, sneezing, allergic rhinitis, and conjunctivitis.

12. The method of claim 7, wherein the at least one of potassium chloride, calcium chloride, and magnesium chloride is at least potassium chloride.

13. A method for treating pain in a subject, comprising:

applying a therapeutically effective amount of a topical composition to skin of the subject;

wherein the topical composition comprises a homogeneous mixture of about 1% to about 10% by volume of a hydrophilic carrier; a therapeutically active ingredient comprising about 0.2% to about 3% by volume of potassium bitartrate and about 0.1% to about 5% by volume of potassium chloride; about 1% to about 20% by volume of at least one essential oil; and about 20% to about 97% by volume of water and at least one of a parasept, a coolant, a perfume, or a surfactant; and wherein the topical composition has been incubated for 24 to 48 hours at 25° C. to 32° C. in a medium of KCl/water.

14. The method of claim 13, wherein the symptoms are at least one of chronic rheumatic pain, pain due to sinus congestion and/or pressure, headaches, ear pressure/pain, premenstrual symptoms, muscle soreness, fibromyalgia, and acute pains due to sprains or strains.

15. The method of claim 13, wherein the at least one essential oil comprises at least one oil derived from lavender, eucalyptus, peppermint, rosemary, patchouli, lemon, sweet orange, clary sage, tea tree, ylang ylang, coconut, olive, castor, menthol, crisp mint, spearmint, or aloe.

16. The method of claim 13, wherein the topical composition is in the form of a liquid, paste, cream, ointment, gel, lotion, spray, soft capsule, solution, pre-treated applicator, or transdermal patch.

17. The method of claim 13, wherein the topical composition consists of the hydrophilic carrier; the potassium bitartrate; the potassium chloride; the at least one essential oil; the water; and the at least one of a parasept, a coolant, a perfume, or a surfactant.

* * * * *